United States Patent
Kodeboina et al.

(10) Patent No.: US 11,025,706 B2
(45) Date of Patent: *Jun. 1, 2021

(54) LOAD-BALANCING SERVER FOR DATA TRANSFORMATION MODULES

(71) Applicant: Atos Digital Health Solutions, Inc., Dallas, TX (US)

(72) Inventors: Kiran Kumar Kodeboina, Freemont, CA (US); Cynthia G. Nicholas, Lake Orion, MI (US); Brenda S. Ikerd, Prairieville, LA (US)

(73) Assignee: ATOS DIGITAL HEALTH SOLUTIONS, INC., Dallas, TX (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/937,489

(22) Filed: Mar. 27, 2018

(65) Prior Publication Data

US 2018/0219942 A1 Aug. 2, 2018

Related U.S. Application Data

(63) Continuation-in-part of application No. 14/885,012, filed on Oct. 16, 2015, now Pat. No. 10,051,047.

(30) Foreign Application Priority Data

Mar. 28, 2017 (EP) .................................... 17163358

(51) Int. Cl.
*H04L 29/08* (2006.01)
*G16H 40/20* (2018.01)
(Continued)

(52) U.S. Cl.
CPC ......... *H04L 67/1002* (2013.01); *G16H 15/00* (2018.01); *G16H 40/20* (2018.01);
(Continued)

(58) Field of Classification Search
None
See application file for complete search history.

(56) References Cited

U.S. PATENT DOCUMENTS 5,557,515 A 9/1996 Abbruzzese et al.
6,115,646 A 9/2000 Fiszman et al.
(Continued)

FOREIGN PATENT DOCUMENTS

EP 0 384 339 A2 8/1990

OTHER PUBLICATIONS

Notice of Allowance dated May 16, 2018 for U.S. Appl. No. 14/8885012.
(Continued)

*Primary Examiner* — Davoud A Zand
(74) *Attorney, Agent, or Firm* — Arc IP Law, PC; Joseph J. Mayo

(57) ABSTRACT

A load-balancing server having at least one memory comprising instructions, at least one processing device configured for executing the instructions and a load-balancing module, coupled to the at least one memory, the at least one processing device, and at least one data transformation module, and configured for determining a first amount of computing resources for allocating to the at least one data transformation module using a load-balancing technique, the at least one data transformation module coupled to the at least one memory, the at least one processing device, and the load-balancing module.

40 Claims, 7 Drawing Sheets

(51) Int. Cl.
*H04L 12/911* (2013.01)
*G16H 15/00* (2018.01)
(52) U.S. Cl.
CPC .......... *H04L 47/70* (2013.01); *H04L 67/1008* (2013.01); *H04L 67/1029* (2013.01)

(56) References Cited

U.S. PATENT DOCUMENTS

| | | | |
|---|---|---|---|
| 7,106,835 B2 | 9/2006 | Saalsaa | |
| 8,447,627 B1 | 5/2013 | Cruise | |
| 8,484,355 B1* | 7/2013 | Lochhead | G06F 9/5072 709/226 |
| 8,612,330 B1* | 12/2013 | Certain | G06F 9/50 705/37 |
| 9,037,631 B2 | 5/2015 | Dietrich et al. | |
| 9,117,002 B1* | 8/2015 | Jenkins | H04L 67/02 |
| 9,137,210 B1* | 9/2015 | Joglekar | H04L 63/0236 |
| 10,333,860 B2* | 6/2019 | Willis | H04L 67/34 |
| 2002/0026329 A1 | 2/2002 | Saito et al. | |
| 2002/0152305 A1 | 10/2002 | Jackson et al. | |
| 2004/0049292 A1 | 3/2004 | Weigand et al. | |
| 2004/0073458 A1 | 4/2004 | Jensen | |
| 2004/0189718 A1 | 9/2004 | Stein et al. | |
| 2005/0066331 A1 | 3/2005 | Inoue et al. | |
| 2005/0108045 A1 | 5/2005 | Gong et al. | |
| 2005/0203771 A1 | 9/2005 | Achan | |
| 2006/0229896 A1 | 10/2006 | Rosen et al. | |
| 2007/0050219 A1 | 3/2007 | Sohr et al. | |
| 2007/0203750 A1 | 8/2007 | Volcheck | |
| 2008/0086327 A1 | 4/2008 | Cox et al. | |
| 2008/0114866 A1* | 5/2008 | Round | G06F 9/50 709/223 |
| 2008/0120462 A1 | 5/2008 | Nehse | |
| 2009/0150534 A1 | 6/2009 | Miller et al. | |
| 2009/0204711 A1* | 8/2009 | Binyamin | H04L 67/1021 709/226 |
| 2011/0276982 A1* | 11/2011 | Nakayama | G06F 9/505 718/105 |
| 2012/0010900 A1 | 1/2012 | Kaniadakis | |
| 2012/0134328 A1 | 5/2012 | Gauvreau et al. | |
| 2014/0074641 A1* | 3/2014 | Wang | H04L 43/08 705/26.3 |
| 2014/0081652 A1 | 3/2014 | Kindworth | |
| 2014/0089511 A1 | 3/2014 | McLean | |
| 2014/0280595 A1 | 9/2014 | Mani et al. | |
| 2015/0020132 A1 | 1/2015 | Willis et al. | |
| 2015/0365462 A1 | 12/2015 | Jenkins et al. | |

OTHER PUBLICATIONS

European Search Report dated Oct. 9, 2017 for EP Application No. 17 163 358.

\* cited by examiner

| 702 | 704 | 706 | 708 | 710 | 712 | 714 | 716 |
|---|---|---|---|---|---|---|---|
| NAME | HISTORY | INPUTTED CLASSIFICATION CODE | SUBMITTED CLASSIFICATION CODE | NARRATIVE | NOTIFICATION | CLARIFICATION | EVALUATION |
| NAME 1 | HISTORY 1 | INPUTTED CLASSIFICATION CODE 1 | SUBMITTED CLASSIFICATION CODE 1 | NARRATIVE 1 | NOTIFICATION 1 | CLARIFICATION 1 | EVALUATION 1 |
| NAME 2 | HISTORY 2 | INPUTTED CLASSIFICATION CODE 2 | SUBMITTED CLASSIFICATION CODE 2 | NARRATIVE 2 | NOTIFICATION 2 | CLARIFICATION 2 | EVALUATION 2 |
| NAME 3 | HISTORY 3 | INPUTTED CLASSIFICATION CODE 3 | SUBMITTED CLASSIFICATION CODE 3 | NARRATIVE 3 | NOTIFICATION 3 | CLARIFICATION 3 | EVALUATION 3 |
| NAME 4 | HISTORY 4 | INPUTTED CLASSIFICATION CODE 4 | SUBMITTED CLASSIFICATION CODE 4 | NARRATIVE 4 | NOTIFICATION 4 | CLARIFICATION 4 | EVALUATION 4 |

FIG. 7

LOAD-BALANCING SERVER FOR DATA TRANSFORMATION MODULES

FIELD OF INVENTION

The present invention relates to the field of data processing and more precisely to load-balancing servers for data transformation modules.

BACKGROUND OF THE INVENTION

Data processing is an important step for the efficient use of information in a lot of areas in general, and particularly in the field of health services, and, especially when the amount of data to process is huge.

For example, when a medical service provider provides a service to a patient, the service provided to the patient may be documented for billing and/or insurance purposes. In some embodiments, the service provided to the patient may be coded into an electronic billing system using one or more classification codes, such as codes associated with the International Statistical Classification of Diseases and Related Health Problems (e.g.,ICD-9 codes and/or ICD-10 codes). These classification codes may enable healthcare professionals and/or an insurance company to correctly identify, document, and/or bill the provided service.

However, as the healthcare industry transitions from utilizing a first set of classification codes to utilizing a second set of classification codes (e.g., from utilizing ICD-9 codes to utilizing ICD-10 codes), medical service providers and/or insurance companies may be faced with a variety of challenges. For example, a medical service provider may incorrectly and/or incompletely code a provided service, particularly if the medical service provider uses the first set of classification codes to code the provided service when coding of the provided service using the second set of classification codes is required by law.

SUMMARY OF THE INVENTION

The present invention has as its object to obviate certain drawbacks of the prior art by offering a means for managing in an efficient way the data processing of information such as for instance the classification code in health services.

This goal is achieved by a load-balancing server for intelligently allocating computing resources to a plurality of computing elements across a computing network in response to an identified demand for computing resources, the load-balancing server comprising an intelligent means for sensing an amount of computing resources accessible by at least one computing element, at least one memory comprising instructions, and at least one processing device configured for executing the instructions, said load-balancing system being characterized in that the instructions, when executed by the at least one processing device, cause the at least one processing device to perform the operations of:

establishing, using a communication unit, a digital communication connection over a computing network between the load-balancing server and a plurality of computing elements in the computing network;

receiving, via the computing network, a request for performing an operation, wherein performing the operation requires utilization of the at least one computing element of the plurality of computing elements;

first determining, based on information comprised in the request, an amount of computing resources required by the at least one computing element to perform the operation;

second determining, based on information received from the intelligent means, an amount of computing resources accessible by the at least one computing element; and allocating, based on the first determining and second determining steps, the amount of computing resources required by the at least one computing element for performing the operation.

According to another feature, the load-balancing server includes one or more modules operatively coupled to and/or utilizing the one or more memories and/or the one or more processors of the load-balancing server for performing particular operations associated with real-time inputting and reviewing, as well as auditing and/or reporting, of information.

According to another feature, the load-balancing server includes at least a first module, a second module, a third module, a fourth module, and/or a fifth module, each module including specially-purposed hardware and/or computer-executable instructions for performing particular operations associated with real-time inputting and reviewing, as well as auditing and/or reporting of information.

According to another feature, the load-balancing server comprises a "queue" memory for storing information such as classification codes, transmitted at least by the first module, placed in queue and waiting to be processed.

According to another feature, the fifth module of the load-balancing server, connected to the queue memory, comprises a module for counting the number of classification codes in queue and transmit said number to an alert module, also includes in said fifth module and, comprising at least a predetermined threshold value, said alert module, thus, determining if the number of inputted classification codes that have been placed in the queue meets and/or exceeds said predetermined threshold value in order to trigger the allocation of computing resources.

According to another feature, the fifth module evaluates by means of a computer-executable program, an amount, based on said predetermined threshold value, of additional processing power required by the first module or the second module or the third module and/or the fourth module for processing inputted classification codes in queue, the evaluated amount(s) of processing power being allocated, by means of the hardware and software-based communication devices of the load-balancing server, to the first module and/or the second module and/or the third module and/or the fourth module.

According to another feature, allocating computing resources include flipping a switch, adjusting processing power, adjusting memory size, partitioning a memory element, controlling one or more input and/or output devices.

According to another feature, a system including the load-balancing server comprises devices and arrangement for real-time inputting and reviewing, as well as auditing and/or reporting, of classification codes associated with provided medical services.

According to another feature, the system includes a communication unit, an I/O (input/output) module, at least one memory for storing data, at least database API and/or at least a processor for the treatment of data.

According to another feature, the system includes one or more user devices each of the user device being utilized by one or more users for performing particular operations associated with real-time inputting and reviewing, as well as auditing and/or reporting, of classification codes associated with provided medical services.

According to another feature, the system includes a first user device, a second user device, a third user device, and/or a fourth user device, each of the user device including at least a memory for storing data, at least a processor for executing computer-executable instructions related to medical services, various input and/or output devices for enabling one or more users to interact with each user device, one or more memories and/or one or more processors.

According to another feature, each of the user devices also includes a keyboard or a mouse or a touchpad or a touchscreen or a camera a microphone, a radio frequency identification (RFID) scanner, a display or a monitor, a speaker, configured to receive input from and/or display output to one or more users and various pieces of hardware for communicating between other user devices and/or with the load-balancing server.

According to another feature, the load-balancing server and/or any user device include one or more radio transceivers or chips or analog front end (AFE) units or antennas or processing units or memory or other logic, and/or other components to implement communication protocols (wired or wireless) and related functionality for facilitating communication between the load-balancing server and/or any of the user devices.

According to another feature, the first user device, the second user device, the third user device and/or the fourth user device communicate with the load-balancing server via one or more networks.

According to another feature, one or more networks include(s) any wireless and/or wired communications network that facilitates communication between the load-balancing server and/or the first user device and/or the second user device and/or the third user device and/or the fourth user device.

According to another feature, the first user utilizes an interactive interface of the first user device to input a classification code associated with a provided medical service and then transmits said classification code from the first user device to the first module of the load-balancing server via the one or more networks at least for storing in the queue.

According to another feature, the first module transmits the inputted classification code and/or the associated narrative to the second user device via the one or more networks for review by the second user on the second user output device to review the inputted classification code for completeness and/or accuracy.

According to another feature, the first module of the load-balancing server and/or the second user device and/or the second module of the load-balancing server and the third user device and/or the third module of the load-balancing server and/or the fourth user device comprise(s) a set of tools that can be configured by means of a computer-executable instructions for automatically performing analyses on notifications and/or classification codes.

According to another feature, said set of tools comprises at least a text and/or code analysis module, a recommendation module and a correction module, said text and/or code analysis module for identifying errors in a given notification and/or classification code and producing an error report containing said errors, said recommendation module for analyzing the error report and producing a recommendation file containing a set of instructions to be executed for correcting the errors identified in the error report, said correction module for reading the recommendation file and modifying said notification and/or classification code.

According to another feature, in the first module of the load-balancing server and/or the second user device, the modified classification code is reviewed prior to submission.

According to another feature, the second user device further comprises an interactive interface enabling the second user to input a notification associated with an inputted classification code, said notification including information associated with the review of the inputted classification code.

According to another feature, the second user device transmits said notification to the second module of the load-balancing server, said second module transmitting said notification to the third user device for review by the third user.

According to another feature, the third user utilizes the one or more output devices of the third user device to review the notification, said one or more output devices generating a report on the review of said notification.

According to another feature, the second module and/or the third user device the modified notification code is reviewed prior to transmission to the first user device.

According to another feature, an arrangement is provided for avoiding transmission of the notification to the first user device until said notification has been reviewed and/or approved by a third user.

According to another feature, the second module of the load-balancing server and/or the third user device and/or the third module of the load-balancing server and/or the fourth user device also includes a data module comprising at least a computer-executable instruction for retrieving, receiving and/or otherwise assessing information stored in one or more databases internal to and/or external to the system, during an analysis of the classification code and/or associated information.

According to another feature, the third user device further comprises an interactive interface for allowing the third user to input a set of information or clarification including information associated with the notification, during and/or after review of the notification.

According to another feature, the clarification is transmitted from the third user device to the second module and/or another module of the load-balancing server for distribution to one or more user devices or transmitted directly to the second user device for review by the second user prior to transmission of the notification to the first user device.

According to another feature, after a submission of the classification code to billing and/or insurance processing, the first module, the second module, and/or any of the first user device, the second user device, and/or the third user device transmits the inputted classification code, the submitted classification code, any information and/or narratives associated with the classification code and/or the provided medical service, the notification, and/or the clarification to the third module and/or the fourth module.

According to another feature, the classification code is randomly selected from an amassed listing and/or database of submitted classification codes by the fourth user, by means of the fourth user device, for auditing purposes.

According to another feature, after auditing information associated with the classification code, the fourth user, by means of the one or more output devices of the fourth user device generates a compliance review report that includes information associated with the completeness, accuracy, and/or compliance of the submitted classification code, as well as an evaluation of the performance of any and all users involved in the coding processes.

According to another feature, the compliance review is transmitted by means of the fourth user device and/or the third module for distribution to any of the first user device, the second user device, and/or the third user device for respective user review.

According to another feature, the report, generated by the fourth module, includes a number of inputted classification codes, a number of submitted classification codes, a number of notifications, a number of clarifications, the information included in said report being sorted based on a variety of factors such as a medical provider type, or a classification code, or a disease diagnosis, or a treatment type, or a hospital, or a notification type, or a clarification type, or a search history.

According to another feature, the report, generated by the fourth module, is transmitted to any of the user devices and/or another system external to the system for review and/or further processing.

According to another feature, the report generated by the fourth module includes a history comprising at least a timestamp associated with an input of a classification code and/or narrative, a timestamp associated with an input of a notification, a timestamp associated with an input of a clarification, a timestamp associated with a submission of a clarification code and a timestamp associated with a compliance review.

According to another feature, the load-balancing server is configured, by means of a control API (Application Programming Interface) included in the system comprising said load-balancing server for processing a high volume of classification codes inputted by a large number of users.

According to another feature, the fifth module of the load-balancing server is configured, by said control API, to manage the allocation of computing resources as they are needed by particular elements of the load-balancing server.

According to another feature, the fifth module includes a specially-purposed hardware for monitoring performance of each element of the load-balancing server, as well as for responding to the computing resource needs of each element.

According to another feature, the fifth module also includes one or more hardware and software-based communication devices to enable communication between said fifth module and at least one of the first module, the second module, the third module, and/or the fourth module.

According to another feature, the load-balancing server comprises a set of modules for transforming data from one form to another form, and/or vice versa, for enabling said load-balancing server to communicate with the user devices, the one or more memories, and/or other devices and/or systems.

According to another feature, the load-balancing server is included in a system comprising a plurality of user devices, each device of the plurality of user devices comprising at least an interactive HMI and/or an API and/or computer-executable instructions utilized by a user for performing particular operations, said plurality of user devices including at least a first user device utilized by a medical service provider for inputting information associated with a provided medical service into the system, a second user device utilized by a coder of medical services for reviewing said information associated with the provided medical service, a third user device utilized by a supervisor for reviewing a notification, based on the review of information associated with the provided medical service, transmitted by the coder of medical services and eventually a fourth user device utilized by an auditor for reviewing at least a clarification, transmitted by the supervisor from the review based on the notification emitted by the coder, and transmitting a compliance review to the load-balancing server for processing.

BRIEF DESCRIPTION OF THE DRAWINGS

Other features and advantages of the present invention will appear more clearly upon reading the following description, given with reference to the appended drawings, in which:

FIG. 7 is a display of a report generated by the fourth module, according to at least one embodiment.

DETAILED DESCRIPTION

Embodiments are directed to a load-balancing server for data processing and more precisely for data transformation modules.

In some embodiments the load-balancing server (102) intelligently allocates computing resources to a plurality of computing elements across a computing network in response to an identified demand for computing resources, the load-balancing server (102) comprising an intelligent means for sensing an amount of computing resources accessible by at least one computing element, at least one memory (104) comprising instructions, and at least one processing device (106) configured for executing the instructions, said load-balancing system being characterized in that the instructions, when executed by the at least one processing device (106), cause the at least one processing device (106) to perform the operations of:

establishing, using a communication unit, a digital communication connection over a computing network between the load-balancing server (102) and a plurality of computing elements in the computing network;

receiving, via the computing network, a request for performing an operation, wherein performing the operation requires utilization of the at least one computing element of the plurality of computing elements;

first determining, based on information comprised in the request, an amount of computing resources required by the at least one computing element to perform the operation;

second determining, based on information received from the intelligent means, an amount of computing resources accessible by the at least one computing element; and allocating, based on the first determining and second determining steps, the amount of computing resources required by the at least one computing element for performing the operation.

Figure 1:
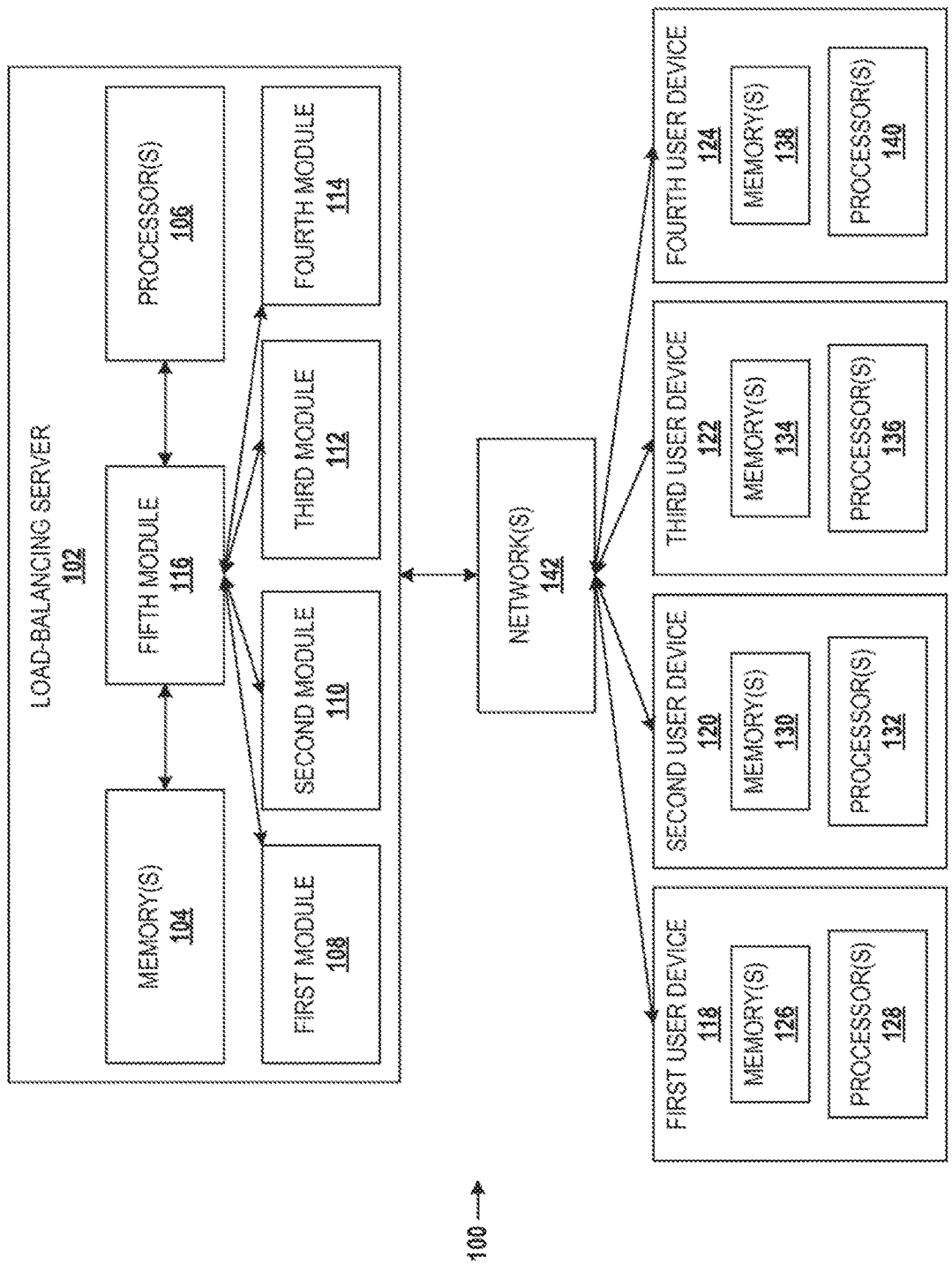
FIG. 1 is a schematic representation of a system comprising a load-balancing server for the data processing, according to at least one embodiment.

The load-balancing server can be used, for example and without limitation, in a system (100, FIG. 1) that comprises devices and arrangement for real-time inputting and reviewing, as well as auditing and/or reporting, of classification codes associated with provided medical services. Multiple users may utilize the system (100) to ensure that each classification code associated with a provided medical service is complete, accurate, and compliant with regulatory laws and guidelines.

For example, after a doctor provides a medical service to a patient, the doctor may utilize the system (100) disclosed herein to input a classification code associated with the medical service provided to the patient. The classification code may include a code associated with the International Statistical Classification of Diseases and Related Health Problems (e.g., ICD-9 codes and/or ICD-10 codes) and may be utilized for billing and/or insurance purposes.

Once inputted and prior to submission of the classification code to formal billing and/or insurance processes, the classification code may be reviewed in real time by a reviewer (e.g., a coder, a billing specialist, and/or the like) to ensure accuracy of the classification code. If the classification code is determined to be incomplete and/or inaccurate, the reviewer may modify the classification code, as well as provide to the doctor a notification identifying any determined issues. The notification may provide the doctor with information to potentially eliminate recurrence of the determined issue(s) when inputting future classification codes. If the classification code is determined to be complete and accurate, the reviewer may submit the classification code to formal billing and/or insurance processes after receiving supervisory approval.

After submission, the classification code may be selected for an auditing process. An auditor may review the classification code inputted by the doctor, the classification code submitted by the reviewer, any determined issue(s) associated with the classification code, any modifications made to the classification code, the notification provided to the doctor, and/or any other information associated with a record of the provided medical service. The auditor may generate a compliance review of the classification code to evaluate completeness and accuracy of the content of the classification code and the notification, as well as performance of the doctor and the reviewer. The auditor may then generate and distribute a report including a variety of analyses associated with the classification code, the notification, the doctor, and/or the reviewer so that future submissions of classification codes continue to become more complete and accurate.

In some embodiments, the system (100) includes a load-balancing server (102), which includes a plurality of servers (102) configured to communicate with one another and/or implement load-balancing techniques, a communication unit, an I/O (input/output) module, at least one memory (104) for storing data, at least a user device API (Application programming interface), at least database API, and/or the like and/or at least a processor (106) for the treatment of data.

The memory (104) may include random access memory (RAM), read only memory (ROM), and/or various forms of secondary storage. RAM may be used to store volatile data and/or to store instructions that may be executed by the processor (106). For example, the data stored may be a command, a current operating state of the load-balancing server (102), an intended operating state of the load-balancing server (102), and/or the like. As a further example, data stored in the memory (104) may include instructions related to various methods and/or functionalities described herein. ROM may be a non-volatile memory device that may have a smaller memory capacity than the memory capacity of a secondary storage. ROM may be used to store instructions and/or data that may be read during execution of computer instructions. Access to both RAM and ROM may be faster than access to secondary storage. Secondary storage may be comprised of one or more disk drives or tape drives and may be used for non-volatile storage of data or as an over-flow data storage device if RAM is not large enough to hold all working data. Secondary storage may be used to store programs that may be loaded into RAM when such programs are selected for execution.

In some embodiments, the memory (104) may include one or more databases for storing medical records, various pieces of information associated with a provided medical service, and/or the like.

In some embodiments, the one or more memories (104) may store any data described herein. Additionally or alternatively, one or more secondary databases located remotely from the load-balancing server (102) may be utilized, accessed, and/or the like.

The one or more processors (106) may control any of the one or more modules and/or functions performed by the various modules in the load-balancing server (102) and/or the one or more user devices. Any actions described as being taken by a processor may be taken by the one or more processors (106) alone or by the one or more processors (106) in conjunction with one or more additional processors and/or modules. Additionally, while only one processor of the one or more processors (106) may be shown, multiple processors may be present. Thus, while instructions may be described as being executed by the one or more processors (106), the instructions may be executed simultaneously, serially, or otherwise by one or multiple processors (106) (and/or processor(s) (128), (132), (136), (140)). The one or more processors (106) may be implemented as one or more computer processing unit (CPU) chips and/or graphical processing unit (GPU) chips and may include a hardware device capable of executing computer instructions. The one or more processors (106) may execute instructions, codes, computer programs, or scripts. The instructions, codes, computer programs, or scripts may be received from the one or more memories(104)(and/or memories(126),(130),(134), (138)), from an I/O module, from a communication unit, and/or the like.

In some embodiments, the load-balancing server (102) may include separate application programming interfaces (APIs) for communicating with the one or more user devices (118), (120), (122), (124), the one or more memories (104), and/or another system and/or device. A mobile device API may provide a connection for communicating with the one or more user devices (118), (120), (122), (124). A database API may provide a connection for communicating with the one or more memories (104) and/or another database. Each API may be associated with a customized physical circuit. The load-balancing server (102) may not include a generic computing system, but instead may include a customized computing system designed to perform the various methods described herein.

The load-balancing server (102) may further include one or more modules (108, 110, 112, 114, 116). For example, the load-balancing server (102) may include a first module (108), a second module (110), a third module (112), a fourth module (114), and/or a fifth module (116).

In some embodiments, each of the first module (108), the second module (110), the third module (112), the fourth module (114), and/or the fifth module (116) may be operatively coupled to and/or utilize the one or more memories (104) and/or the one or more processors (106) of the load-balancing server for performing particular operations associated with real-time inputting and reviewing, as well as auditing and/or reporting, of classification codes associated with provided medical services. Each of the first module (108), the second module (110), the third module (112), the fourth module (114), and/or the fifth module (116) may also include specially-purposed hardware and/or computer-executable instructions for performing particular operations associated with real-time inputting and reviewing, as well as auditing and/or reporting, of classification codes associated with provided medical services. The load-balancing server (102) may be configured to receive, retrieve, transmit, store, delete, modify, and/or otherwise transform any information described herein.

The system (100) may include one or more user devices. For example, the system (100) may include a first user device (118), a second user device (120), a third user device (122), and/or a fourth user device (124). Each of the first user device (118), the second user device (120), the third user device (122), and/or the fourth user device (124) may be utilized by one or more users for performing particular operations associated with real-time inputting and reviewing, as well as auditing and/or reporting, of classification codes associated with provided medical services. For example, the first user device (118) may include one or more memories (126) and/or one or more processors (128); the second user device (120) may include one or more memories (130) and/or one or more processors (132); the third user device (122) may include one or more memories (134) and/or one or more processors (136); and/or the fourth user device (124) may include one or more memories (138) and/or one or more processors (140).

In some embodiments, components of each of the first user device (118), the second user device (120), the third user device (122), and/or the fourth user device (124) may include one or more similar elements as those described above (e.g., a communication unit, APIs, and/or the like) as being included, in some embodiments, in the load-balancing server (102).

Each of the first user device (118), the second user device (120), the third user device (122), and/or the fourth user device (124) may also include various input and/or output devices for enabling one or more users to interact with each user device. For example, each of the user devices (118), (120), (122), (124) may include a keyboard, a mouse, a touchpad, a touch-screen, a camera, a microphone, a radio frequency identification (RFID) scanner, a display, a monitor, a speaker, and/or the like configured to receive input from and/or display output to one or more users. Each of the user devices (118), (120), (122), (124) may also include various pieces of hardware for communicating between other user devices and/or with the load-balancing server.

The load-balancing server (102) and/or any user device (118), (120), (122), (124) may include one or more radio transceivers, chips, analog front end (AFE) units, antennas, processing units, memory, other logic, and/or other components to implement communication protocols (wired or wireless) and related functionality for facilitating communication between the load-balancing server (102) and/or any of the user devices (118), (120), (122), (124). As a further example, a communication unit may include modems, modem banks, Ethernet devices, universal serial bus (USB) interface devices, serial interfaces, token ring devices, fiber distributed data interface (FDDI) devices, wireless local area network (WLAN) devices or device components, radio transceiver devices such as code division multiple access (CDMA) devices, global system for mobile communications (GSM) radio transceiver devices, universal mobile telecommunications system (UMTS) radio transceiver devices, long term evolution (LTE) radio transceiver devices, worldwide interoperability for microwave access (WiMAX) devices, and/or other devices for communication. Communication protocols may include WiFi, Bluetooth®, WiMAX, Ethernet, powerline communication (PLC), and/or the like.

In some embodiments, communicating between any of the devices (e.g., the load-balancing server (102) and/or the user devices (118), (120), (122), (124)) may include transforming and/or translating data from being compatible with a first communication protocol to being compatible with a second communication protocol.

Further, each of the first user device (118), the second user device (120), the third user device (122), and/or the fourth user device (124) may communicate with the load-balancing server (102) via one or more networks (142).

In some embodiments, the one or more networks (142) may include any wireless and/or wired communications network that facilitates communication between the load-balancing server (102) the first user device (118), the second user device (120), the third user device (122), and/or the fourth user device (124). For example, the one or more networks may include an Ethernet network, cellular network, a computer network, the Internet, a Wi-Fi network, a Bluetooth network, an RFID network, an NFC network, and/or the like.

In some embodiments, a first user may include a medical service provider. For example, the first user may include a doctor, a dentist, a surgeon, a specialist, a physician's assistant, a nurse, and/or any other medical professional. Additionally, the first user may also include an administrator of a medical service provider, an assistant, and/or the like. In some embodiments, the first user may include multiple users.

In some embodiments, a second user may include a coder of medical services. For example, the second user may include a billing specialist or coordinator, an accountant, an administrator of a medical service provider, a client relationship liaison, and/or the like. In some embodiments, the second user may include multiple users.

In some embodiments, a third user may include a supervisor of the second user. For example, the third user may include a billing manager, an account manager, an administrator of a medical service provider, a client relationship manager, and/or the like.

In some embodiments, the third user may include multiple users.

In some embodiments, a fourth user may include an auditor. For example, the fourth user may include a third party auditor, an internal auditor, an analyst, an administrator of a medical service provider, and/or the like.

In some embodiments, the fourth user may include multiple users.

After a medical service (e.g., an office visit, a consultation, an operation, therapy, and/or the like) has been provided to a patient, the provided medical service (and/or a diagnosis associated with the provided medical service) may be documented and/or otherwise recorded for billing and/or insurance purposes. Accordingly, the first user may utilize an interactive interface of the first user device (118) to input a classification code associated with a provided medical service. For example, the first user may input a particular classification code, such as an ICD-10 code associated with the provided medical service and/or a written narrative describing details of the provided medical service, using the one or more input devices included in the first user device (118) described above.

In some embodiments, inputting the classification code may also include inputting a plurality of classification codes, inputting information associated with the provided medical service and/or the patient such as demographic information, patient information, contact information, and/or the like. The inputted classification code may be received by the first user device (118) and then transmitted from the first user device (118) to the first module (108) of the load-balancing server (102) via the one or more networks (142).

After receiving the inputted classification code, the first module (108) may store the inputted classification code in the one or more memories (104). The first module (108) may also input the inputted classification code into a queue of classification codes that are to be processed and/or submitted via the system (100).

Prior to formal submission of the inputted classification code, the first module (108) may transmit the inputted classification code and/or the associated narrative (e.g., any information associated with the provided medical service such as medical record information, patient information, and/or the like) to the second user device (120) via the one or more networks (142) for review by the second user. The second user may utilize the one or more output devices of the second user device (120) to review the inputted classification code. For example, the second user may analyze the inputted classification code for completeness and/or accuracy.

If the second user determines that the inputted classification code is incomplete and/or inaccurate, or requires updating from a first set of codes to a second set of codes, the second user may modify, delete, add, and/or replace the inputted classification code with a second classification code using the second user device (120). For example, the second user may determine that the inputted classification code includes an out-of-date (and/or otherwise noncompliant) ICD-9 code, and thus may replace the ICD-9 code with an ICD-10 code using the second user device (120). As another example, the second user may determine that the inputted classification code does not include an ICD-10 code and instead only includes a written narrative describing the provided medical service, and thus may select a corresponding ICD-10 code using the second user device (120). As a third example, the second user may determine that the inputted classification code is incomplete, and thus may request additional information from the first user so that an appropriate classification code may be selected.

Conversely, if the second user determines that the inputted classification code is complete and/or accurate, then the second user may provide approval of the inputted classification code using the second user device (120).

In some embodiments, approval of the classification code may be required from a plurality of second users prior to submission of the classification code.

In some embodiments, the first module (108) and/or the second user device (120) comprises a set of tools that can be configured by means of a computer-executable instructions for automatically performing analyses of the inputted classification code. For example and without limitation, the set of tools may comprises at least a text and/or code analysis module for identifying errors in a given inputted classification code and/or a provided narrative and producing an error report containing said errors. The error report is then transmitted, by means of a communication device, to a recommendation module, included in the set of tools. Said recommendation module analyzes the error report and produces a recommendation file containing a set of instructions to implement for correcting the errors identified in the error report. The recommendation file is, then, transmitted to a correction module also included in the set of tools, by means of a communication means. The correction module reads the recommendation file and modifies the inputted classification code to the second user device (120) for review prior to submission of the classification code. The first module (108) and/or the second user device (120) may also comprises a data module comprising computer-executable instructions for retrieving, receiving, and/or otherwise accessing information stored in one or more databases internal to and/or external to the system (100), during an analysis of the inputted classification code.

During and/or after review of the inputted classification code, the second user device (120) may further comprises a set of tools for enabling the second user to input a notification associated with the inputted classification code.

In some embodiments, the notification may include information associated with the review of the inputted classification code. For example, the notification may identify any errors identified during the review of the classification code and/or any modifications of the classification code.

In some embodiments, the notification may include comments, notes, identification of errors, and/or recommendations of modifications associated with the inputted classification code and/or other inputted information. As used herein, comments may include any of the aforementioned information types, as well as text, numerical data, and/or the like.

Once inputted, the notification may be transmitted from the second user device (120) to the second module (108) of the load-balancing server (102). Accordingly, the second module (110) may receive the notification from the second user device (120). After receipt and prior to submission of the classification code, the second module (110) may transmit the notification to the third user device (122) for review by the third user. Alternatively, the notification may be transmitted directly from the second user device (120) to the third user device (122).

In some embodiments, the third user may utilize the one or more output devices of the third user device (122) to review the notification. For example, the third user, by means of the third user device (122), may analyze the notification for completeness and/or accuracy to ensure that information included in the notification and provided by second user is complete and accurate prior to transmission of the notification to the first user device (118) for review by the first user.

If, from the analysis of the notification by said third user device (122), the third user determines that information included in the notification is incomplete and/or inaccurate, said third user may modify, delete, add, and/or replace one or more pieces of information included in said notification, by means of said third user device (122). For example, the analysis of the notification by said third user device (122) may reveal, for example in a report generated by the one or more output devices, that the notification includes information indicating that the second user updated a noncompliant ICD-9 code with an incorrect ICD-10 code. The third user, after reviewing the report generated by the one or more output devices, may replace and/or suggest replacement of the incorrect ICD-10 code with a correct ICD-10 code using the third user device (122).

Conversely, if the analysis of the notification by said third user device (122) determines that the notification is complete and/or accurate, then the third user, by reviewing the report generated by the one or more output devices, may provide approval of the notification by using said third user device (122).

In some embodiments, approval of the notification may be required from a plurality of third users prior to transmission of the notification to the first user and/or submission of the classification code for billing and/or insurance processing.

In some embodiments, the second module (110) and/or the third user device (122) comprises a set of tools that can be configured by means of a computer-executable instructions for automatically performing analyses on notifications and/or classification codes. For example and without limitation, the set of tools comprises at least a text and/or code analysis module for identifying errors in a given notification and/or the classification code (as well as any associated information and/or narrative) and producing an error report containing said errors. The error report is then transmitted, by means of a communication device, to a recommendation module, included in the set of tools. Said recommendation module analyzes the error report and produces a recommendation file containing a set of instructions to implement for correcting the errors identified in the error report. The recommendation file is, then, transmitted to a correction module also included in the set of tools, by means of a communication means. The correction module reads the recommendation file and modifies the notification, for example, to the third user device (122) for review prior to transmission of the notification to the first user device (118). The second module (110) and/or the third user device (122), may also comprises a data module comprising computer-executable instructions for retrieving, receiving, and/or otherwise accessing information stored in one or more databases internal to and/or external to the system (100), during an analysis of the inputted classification code.

The third user device (122) may further comprises an interactive interface, allowing the third user to input a set of information or clarification associated with the notification, during and/or after review of the notification.

In some embodiments, the clarification may include information associated with the review of the notification. For example, the clarification may identify any errors identified during the review of the notification and/or any modifications of the classification code. The clarification may also provide approval of the notification and/or the classification code.

The clarification may be transmitted from the third user device (122) to the second module (110) and/or another module of the load-balancing server (102) for distribution to one or more user devices, or may be transmitted directly to the second user device (120) for review by the second user prior to transmission of the notification to the first user device (118).

The second user device (120) may receive the clarification from either from the second module (110) and/or the third user device (122). The second user may utilize the one or more output devices of the second user device (122) to review the clarification. In this manner, the clarification may provide to the second user information associated with the review of the notification. The second user may utilize the second user device (122) to approve and/or modify the notification and/or the classification code based on information included in the clarification. The second user may use information included in the clarification to improve future notification inputs, avoid particular notification and/or coding errors, and/or the like. Ultimately, providing the second user with the clarification prior to transmission of the notification to the first user device (118) and/or submission of the classification code may increase completeness and/or accuracy of future notification and/or classification code inputs. The second user may then, using the second user device (120), the first module (109), and/or the second module (110), submit the classification code for billing and/or insurance processing.

Additionally, once approved by the second user and/or the third user, the notification may then be transmitted to the first user device (118). The first user device (118) may receive the notification from either from the first module (108), the second module (110), the second user device (120), and/or the third user device (122). The first user may utilize the one or more output devices of the first user device (118) to review the notification. In this manner, the notification may provide to the first user information associated with the review of the inputted classification code. The first user may also use information included in the notification to improve future classification code inputs, avoid particular coding errors, and/or the like. Ultimately, providing the first user with the notification may increase completeness and/or accuracy of future classification code inputs. Further, because the inputted classification code, any associated information and/or narrative, the notification, and/or the clarification may all be processed as described herein prior to submission of the classification code for billing and/or insurance purposes, these processes may take place in real time and/or near real time.

After submission of the classification code to billing and/or insurance processing, the first module (108), the second module (110), and/or any of the first user device (118), the second user device (120), and/or the third user device (122) may transmit the inputted classification code, the submitted classification code, any information and/or narratives associated with the classification code and/or the provided medical service, the notification, and/or the clarification to the third module (112) and/or the fourth module (114).

In some embodiments, the classification code may be randomly selected from an amassed listing and/or database of submitted classification codes by the fourth user by means of the fourth user device (124) for auditing purposes. In response, the third module (112) may comprises a set of tools for transmitting information associated with the classification code to the fourth user device (124) for auditing. The fourth user device (124) may receive said information, and the fourth user may utilize the one or more output devices of the fourth user device (124) to review this information. For example, the fourth user, by means of the fourth user device (124), may analyze the classification code and all associated information (e.g., the notification, the clarification, and/or the like) for completeness, accuracy, and/or compliance with regulatory guidelines and/or laws to ensure that the classification code, as well as the reviewing processes described herein, is complete, accurate, and/or compliant with regulations. As a product of this review, the fourth user, by means of the one or more output devices of the fourth user device (124) may generate a compliance review that includes information associated with the completeness, accuracy, and/or compliance of the submitted classification code, as well as an evaluation of the performance of any and all users involved in the coding processes (e.g., the first user, the second user, and/or the third user).

In some embodiments, a predetermined percentage of all submitted classification codes may be audited at random.

If, during review and/or analysis of the classification code, by means of the fourth user device (124), the fourth user determines that the submitted classification code is incomplete, inaccurate, and/or otherwise noncompliant, the fourth user may, by using said fourth user device (124), input information indicating any identified errors. Conversely, if the analysis of the classification code by the fourth user device, reveals that the submitted classification code is complete, accurate and/or otherwise compliant, then the fourth user may, by using said fourth user device (124), provide approval submitted classification code.

In some embodiments, the fourth user may, by using the fourth user device (124), provide comments regarding coding regulations, suggestions for improving efficiency of the coding process, performing grades and/or scores associated with a level of achieved performance of each user involved in the coding process, and/or the like.

In some embodiments, the provided input may be included in the compliance review of the classification code.

In some embodiments, the third module (112) and/or the fourth user device (124) comprises a set of tools that can be configured by means of a computer-executable instructions for automatically performing analyses on notifications and/or classification codes. For example and without limitation, the set of tools comprises at least a text and/or code analysis module for identifying errors in a given classification code (as well as any associated information, narrative, notification, clarification, and/or the like), and producing an error report containing said errors. The error report is then transmitted, by means of a communication means, to a recommendation module included in the set of tools. The recommendation module comprise a set of instructions to analyze the error report and produce a recommendation file containing a second set of instructions to be executed -for correcting the errors identified in the error report. The recommendation file is, then, transmitted to a correction module also included in the set of tools, by means of a communication device. The correction module reads the recommendation file and modifies, for example, the classification code in order to allow the coding process to result in a more complete, accurate, compliant, and/or otherwise efficient coding of the provided medical service. The compliance review generated by the one or more output devices of the fourth user devices (124), may also include the information contained in the recommendation file, for example information on the completeness, the compliance, etc. The third module (112) and/or the fourth user device (124) may also comprises data module comprising computer-executable instructions for retrieving, receiving, and/or otherwise accessing information stored in one or more databases internal to and/or external to the system (100), during an analysis of the submitted classification code and/or its associated information described herein.

In some embodiments, the compliance review may be transmitted from the fourth user device (124) and/or the third module (112) for distribution to any of the first user device (118), the second user device (120), and/or the third user device (122) for respective user review.

In some embodiments, the fourth user (and/or another user) may utilize the fourth module (114) to generate a report associated with the classification code. For example, the report may include a summary, charts, graphs, and/or analytics based on the coding process of the submitted classification code.

In some embodiments, the fourth module (114) may utilize information associated with the first user, the second user, the third user, the fourth user, the inputted classification code, the submitted classification code, the notification, the clarification, the compliance review, and/or any other information associated with the provided medical service to generate the report.

In some embodiments, the report may include a number of inputted classification codes, a number of submitted classification codes, a number of notifications, a number of clarifications, and/or the like information included in the report may be sorted based on a variety of factors such as a medical provider type, a classification code, a disease diagnosis, a treatment type, a hospital, a notification type, a clarification type, a search history, and/or the like. The report may be transmitted from the fourth module (114) to any of the user devices (118), (120), (122), (124) and/or another system external to the system (100) for review and/or further processing.

In some embodiments, the load-balancing server (102) may be configured, by means of a control API (Application Programming Interface) included in the system (100) comprising said load-balancing server (102), for processing a high volume of classification codes inputted by a large number of users. As such, limited computing resources of the load-balancing server (102) such as memory, processing power, and/or the like may be in high demand at various times during processing. Accordingly, the fifth module (116) may be configured, by said control API, to manage the allocation of computing resources as they are needed by particular elements (e.g., the one or more memories (104), the one or more processors (106), and/or the one or more modules (108), (110), (112), (114), (116)) of the load-balancing server (102). In some embodiments, the fifth module (116) may include specially-purposed hardware for monitoring performance of each element of the load-balancing server (102), as well as for responding to the computing resource needs of each element. For example, the fifth module (116) may include and/or be included in a load-balancing server separate and distinct from the load-balancing server (102).

In some embodiments, the fifth module (116) may also include one or more hardware and software-based communication devices (for example and without limitation routers, modems, etc.) to enable communication between the fifth module (116) and at least one of the first module (108), the second module (110), the third module (112), and/or the fourth module (114).

The load-balancing server (102) may comprise, for example, a "queue" memory for storing information such as classification codes, transmitted for instance by the first module (108), placed in queue and waiting to be processed. The fifth module (116) of the load-balancing server (102), connected to the queue memory, may comprise a module for counting the number of classification codes in queue and transmit said number to an alert module, also includes in said fifth module (116) and, comprising at least a predetermined threshold value. The alert module, thus, determines if the number of inputted classification codes that have been placed in the queue meets and/or exceeds said predetermined threshold value in order to trigger the allocation of computing resources. Based on determining that the number of inputted classification codes in the queue meets and/or exceeds the predetermined threshold value, the fifth module (116) may evaluate, by means of a computer-executable program, an amount of additional processing power required by the first module (108), the second module (110), the third module (112), and/or the fourth module (114) for processing the inputted classification codes in the queue. The fifth module (116) may then, by means of the one or more hardware and software-based communication devices, allocate the evaluated amount(s) of processing power to the first module (108), the second module (110), the third module (112), and/or the fourth module (114).

In some embodiments, factors affecting the allocation of computing resources by the fifth module (116) may include a volume of classification codes to be processed by the load-balancing server (102), a duration of time during which computing resources are required by one or more elements of the load-balancing server (102), and/or the like.

In some embodiments, computing resources may be allocated to and/or distributed amongst a plurality of load-balancing servers (102) included in the load-balancing server (102) based on one or more factors.

In some embodiments, allocating computing resources may include flipping a switch, adjusting processing power, adjusting memory size, partitioning a memory element, controlling one or more input and/or output devices, and/or the like. For example, additional memory in the one or more memories (104) may be allocated for use by a particular data transformation module that requires additional memory in order to effectively process a high volume of classification codes.

In some embodiments, the load-balancing server (102) may utilize parallel processing techniques such as dedicating a plurality of processors included in the one or more processors (106) for processing a high volume of classification codes by a particular data transformation module of the load-balancing server (102). The load-balancing server (102) may also transmit data to another system and/or a second load-balancing server for processing.

In some embodiments, inputted classification codes and/or associated information may be received by the load-balancing server (102) (and/or one or more modules of the load-balancing server (102) in a first format. The load-balancing server (102) may convert the inputted classification codes and/or associated information from the first format to a second format prior to processing and/or storage.

In some embodiments, inputted classification codes and/or associated information that is transmitted between one or more elements of the system (100) may be encoded, encrypted, decoded, decrypted, and/or the like. An encryption key used to encrypt data, for example, may be transmitted substantially simultaneously to any transmission of data so that a receiving device may decrypt encrypted data.

In some embodiments, the load-balancing server (102) may comprise a set of modules for transforming data from one form (e.g., a user device communication protocol) to another form (e.g., a database communication protocol), and/or vice versa, for enabling said load-balancing server (102) to communicate with the user devices, the one or more memories (104), and/or other devices and/or systems.

In some embodiments, a dashboard interface and/or similar portal may be provided by the system (100) containing the load-balancing server (102). One or more users may access the dashboard interface using one or more of the user devices described herein and/or another device. User authentication, such as single and/or dual authentication, may be required for a user to access the dashboard interface.

Figure 2:
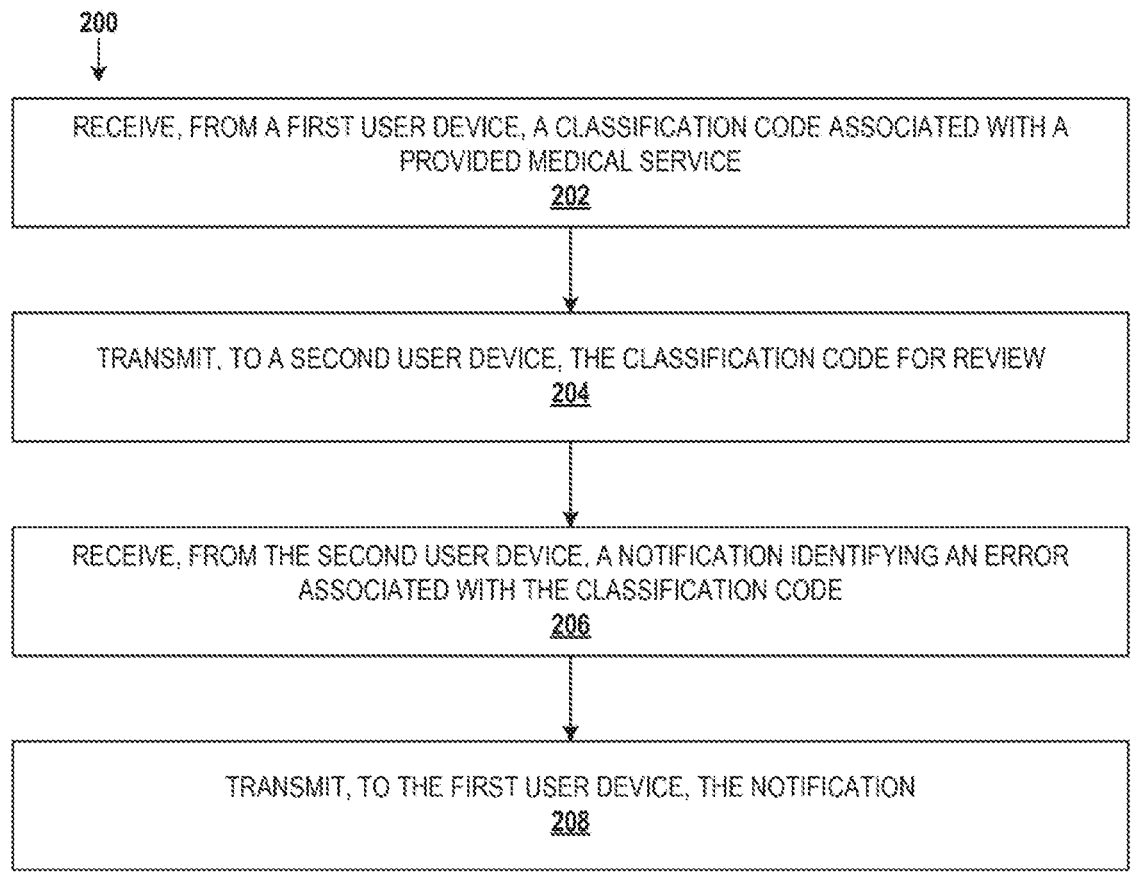
FIG. 2 represents the steps of the data processing executed by the first module of the system comprising a load-data balancing server, according to at least one embodiment.

FIG. 2 shows an exemplary of a method (200) for performing operations associated with the first module (108), by using the load-balancing server (102) (e.g., the first module 108), the first user device (118), and/or the second user device (120). For example and without limitation, said method may include the steps of:

receiving (200), from the first user device, a classification code associated with a provided medical service. For example, the first user (e.g., a medical provider) may input information (e.g., a classification code, a narrative, and/or other information) associated with a provided medical service into the system (100) using the first user device (118), which then transmits the inputted information to the load-balancing server (102) for processing by the first module (108).

transmitting (204), to the second user device, the classification code for review. For example, the first module (108) may transmit the inputted information associated with the provided medical service to the second user device (120) for review by the second user (e.g., a coder).

receiving (206), from the second user device, a notification identifying an error associated with the classification code. For example, the second user, using the second user device (120), may review the inputted information to identify one or more errors associated with an inputted classification code and/or narrative. The notification may be generated by the second user device (120) after review of the inputted information is complete. The notification may be transmitted from the second user device (120) to the load-balancing server (102) for processing by the first module (108) (and/or any other module described herein).

transmitting (208), to the first user device, the notification. For example, the first module (108), upon receipt of the notification from the second user device (120), may transmit the notification to the first user device (118) so that the first user may review the notification. In this manner, comments, notes, identification of one or more errors, and/or recommendations of modifications associated with the inputted information is provided to the first user so that the first user may learn and improve subsequent information inputs. As described herein, the notification may not be transmitted to the first user device (118) until it has been reviewed and/or approved by a third user (and/or any other user). An arrangement may be provided for avoiding the transmission of said notification.

Figure 3:
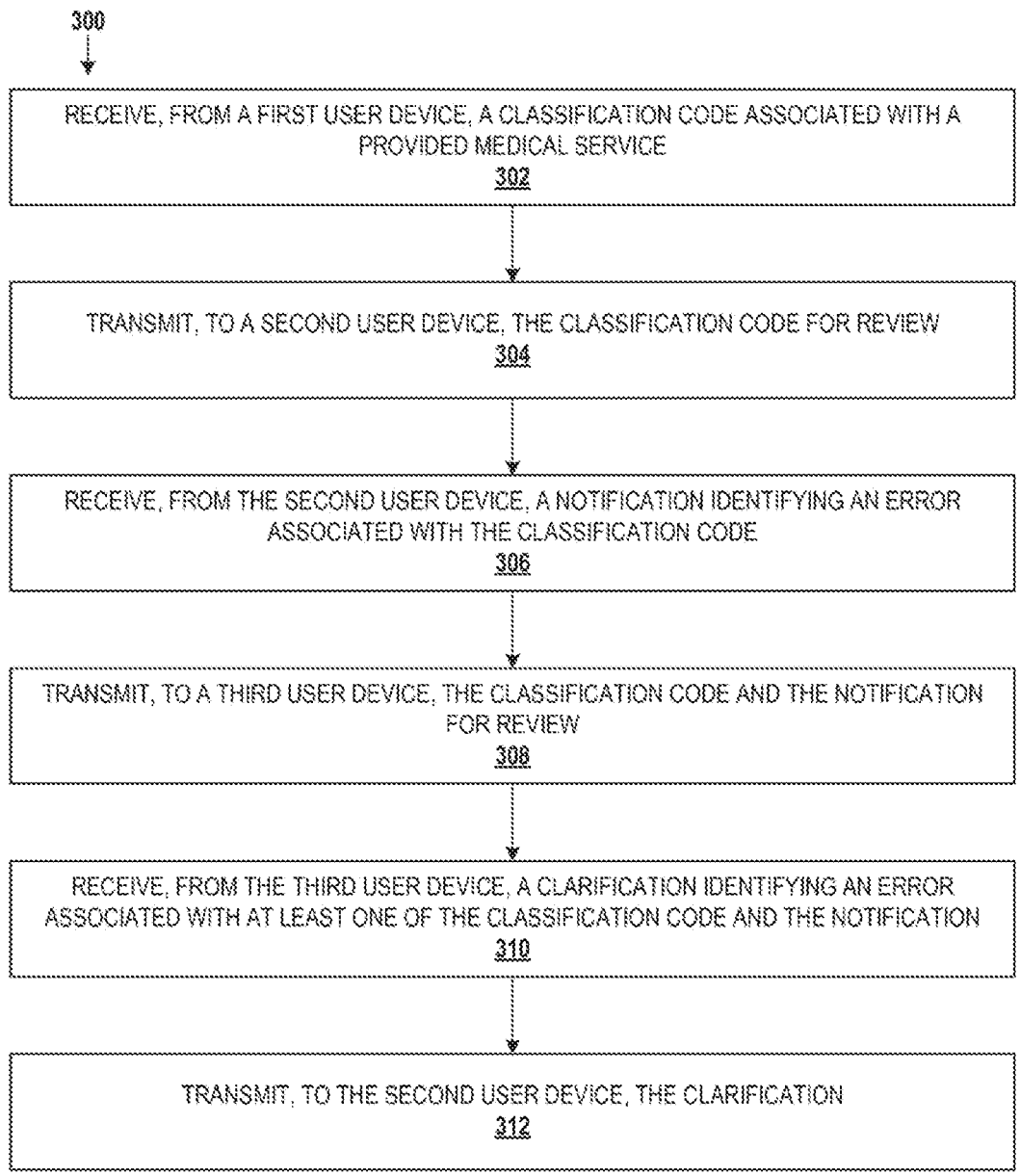
FIG. 3 represents the steps of the data processing executed by the second module, according to at least one embodiment.

FIG. 3 shows an exemplary of a method (300) for performing operations associated with the second module (110), by using the load-balancing server (102) (e.g., the first module (108) and/or the second module(110), the first user device (118), the second user device (120), and/or the third user device (122). For example and without limitation, said method may include the steps of:

receiving (302), from the first user device, a classification code associated with a provided medical service. For example, the first user (e.g., a medical provider) may input information (e.g., a classification code, a narrative, and/or other information) associated with a provided medical service into the system (100) using the first user device (118), which then transmits the inputted information to the load-balancing server (102) for processing by the first module (108).

transmitting (304), to the second user device, the classification code for review. For example, the first module (108) may transmit the inputted information associated with the provided medical service to the second user device (120) for review by the second user (e.g., a coder).

receiving (306), from the second user device, a notification identifying an error associated with the classification code. For example, the second user, using the second user device (120), may review the inputted information to identify one or more errors associated with an inputted classification code and/or narrative. The notification may be generated by the second user device (120) after review of the inputted information is complete. The notification may be transmitted from the second user device (120) to the load-balancing server (102) for processing by the first module (108) and/or the second module (110) (and/or any other module described herein).

transmitting (308), to a third user device, the classification code and the notification for review. For example, the second module (110), upon receipt of the notification, may transmit the notification to the third user device (122) for review by the third user (e.g., a supervisor).

receiving (310), from the third user device, a clarification identifying an error associated with at least one of the classification code and the notification. For example, the third user, using the third user device (122), may review the inputted information and/or the generated notification to identify one or more errors associated with an inputted classification code, a narrative, and/or the notification (e.g., comments associated with the inputted information and provided by the second user). The clarification may be generated by the third user device (122) after review of the inputted information and/or the notification is complete. The clarification may be transmitted from the third user device (122) to the load-balancing server (102) for processing by the first module (108), the second module (110), and/or the third module (112) (and/or any other module described herein).

transmitting (312), to the second user device, the clarification. For example, the second module (110), upon receipt of the clarification from the third user device (122), may transmit the clarification to the second user device (120) so that the first user may review the clarification. In this manner, the clarification (e.g., comments associated with the inputted information and/or the notification) is provided to the second user so that the second user may learn from the clarification and improve subsequent information inputs, modifications, notification inputs, and/or the like. As described herein, the clarification may not be transmitted to the second user device (120) until it has been reviewed and/or approved by the third user (and/or another user).

In some embodiments, the clarification is transmitted to the second user device (120) prior to transmission of the notification to the first user device (118) so that the second user has an opportunity to review, modify, and/or otherwise update the notification with information provided in the clarification. After the second user has reviewed the clarification and performed any necessary modifications to the inputted information, the inputted information (e.g., the inputted classification code) may be submitted to the load-balancing server (102) for billing and/or insurance processing.

Figure 4:
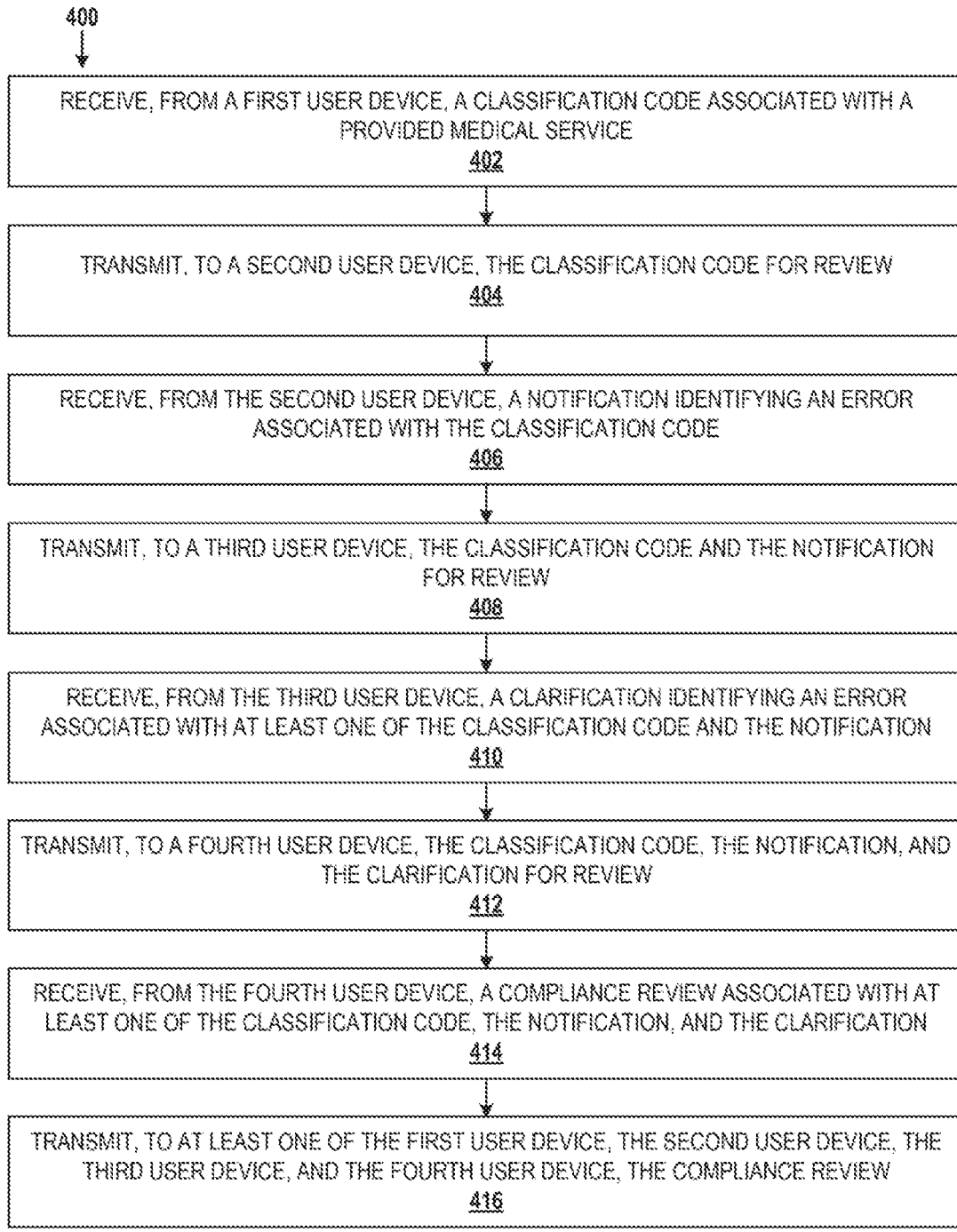
FIG. 4 represents the steps of the data processing executed by the third module, according to at least one embodiment.

FIG. 4 shows an exemplary of a method (400) for performing operations associated with the third module (112), by using the load-balancing server (102) (e.g., the first module (108), the second module (110), and/or the third module (112)), the first user device (118), the second user device (120), the third user device (122), and/or the fourth user device (124). For example and without limitation, said method may include the step of:

receiving (402), from the first user device, a classification code associated with a provided medical service. For example, the first user (e.g., a medical provider) may input information (e.g., a classification code, a narrative, and/or other information) associated with a provided medical service into the system (100) using the first user device (118), which then transmits the inputted information to the load-balancing server (102) for processing by the first module (108).

transmitting (404), to the second user device, the classification code for review. For example, the first module (108) may transmit the inputted information associated with the provided medical service to the second user device (120) for review by the second user (e.g., a coder).

receiving (406), from the second user device, a notification identifying an error associated with the classification code. For example, the second user, using the second user device (120), may review the inputted information to identify one or more errors associated with an inputted classification code and/or narrative. The notification may be generated by the second user device (120) after review of the inputted information is complete. The notification may be transmitted from the second user device (120) to the load-balancing server (102) for processing by the first module (108) and/or the second module (110) (and/or any other module described herein).

transmitting (408), to a third user device, the classification code and the notification for review. For example, the second module (110), upon receipt of the notification, may transmit the notification to the third user device (122) for review by the third user (e.g., a supervisor).

receiving (410), from the third user device, a clarification identifying an error associated with at least one of the classification code and the notification. For example, the third user, using the third user device (122), may review the inputted information and/or the generated notification to identify one or more errors associated with an inputted classification code, a narrative, and/or the notification (e.g., comments associated with the inputted information and provided by the second user). The clarification may be generated by the third user device (122) after review of the inputted information and/or the notification is complete. The clarification may be transmitted from the third user device (122) to the load-balancing server (102) for processing by the first module (108), the second module (110), and/or the third module (112) (and/or any other module described herein).

transmitting (412), to a fourth user device, the classification code, the notification, and/or the clarification for review. For example, the third module (112), upon receipt of the clarification from the third user device (122), may transmit the inputted information, the notification, and/or the clarification to the fourth user device (124) for review by the fourth user (e.g., an auditor).

receiving (414), from the fourth user device, a compliance review identifying an error associated with at least one of the classification code, the notification, and the clarification. For example, the fourth user, using the fourth user device (124), may review the inputted information and/or the generated notification to identify one or more errors associated with an inputted classification code, a narrative, the notification (e.g., comments associated with the inputted information and provided by the second user), and/or the clarification (e.g., comments associated with the notification and provided by the third user). The compliance review may be generated by the fourth user device (124) after review of the inputted information, the notification, and/or the clarification is complete. The compliance review may be transmitted from the fourth user device (124) to the load-balancing server (102) for processing by the first module (108), the second module (110), the third module (112), and/or the fourth module (114) (and/or any other system).

transmitting (416), to at least one of the first user device, the second user device, the third user device, and the fourth user device, the compliance review. For example, the third module (112) may transmit the compliance review to one or more of the first user device (118), the second user device (120), the third user device (122), and/or the fourth user device (124) for review by respective users of said user devices.

Figure 5:
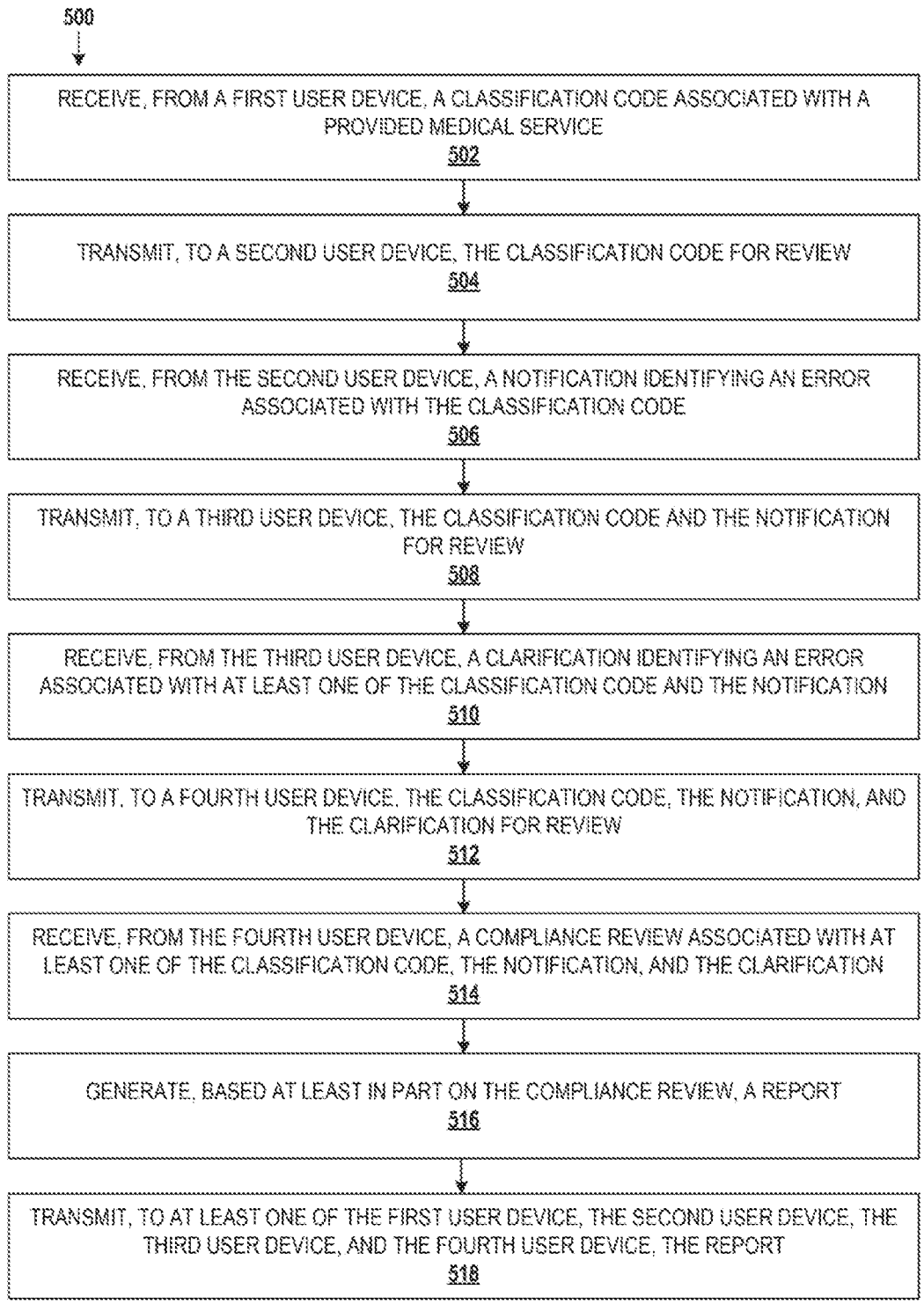
FIG. 5 represents the steps of the data processing executed by the fourth module, according to at least one embodiment.

FIG. 5 shows an exemplary of a method (500) for performing operations associated with the fourth module (114), by using the load-balancing server (102) (e.g., the first module (108), the second module (110), the third module (112), and/or the fourth module (114)), the first user device (118), the second user device (120), the third user device (122), and/or the fourth user device (124). For example and without limitation, said method may include the steps of:

receiving (502), from the first user device (118), a classification code associated with a provided medical service. For example, the first user (e.g., a medical provider) may input information (e.g., a classification code, a narrative, and/or other information) associated with a provided medical service into the system (100) using the first user device (118), which then transmits the inputted information to the load-balancing server (102) for processing by the first module (108).

transmitting (504), to the second user device, the classification code for review. For example, the first module (108) may transmit the inputted information associated with the provided medical service to the second user device (120) for review by the second user (e.g., a coder).

receiving (506), from the second user device, a notification identifying an error associated with the classification code. For example, the second user, using the second user device (120), may review the inputted information to identify one or more errors associated with an inputted classification code and/or narrative. The notification may be generated by the second user device (120) after review of the inputted information is complete. The notification may be transmitted from the second user device (120) to the load-balancing server (102) for processing by the first module (108) and/or the second module (110) (and/or any other module described herein).

transmitting (508), to a third user device, the classification code and the notification for review. For example, the second module (110), upon receipt of the notification, may transmit the notification to the third user device (122) for review by the third user (e.g., a supervisor).

receiving (510), from the third user device, a clarification identifying an error associated with at least one of the classification code and the notification. For example, the third user, using the third user device (122), may review the inputted information and/or the generated notification to identify one or more errors associated with an inputted classification code, a narrative, and/or the notification (e.g., comments associated with the inputted information and provided by the second user). The clarification may be generated by the third user device (122) after review of the inputted information and/or the notification is complete. The clarification may be transmitted from the third user device (122) to the load-balancing server (102) for processing by the first module (108), the second module (110), and/or the third module (112) (and/or any other module described herein).

transmitting (512), to a fourth user device, the classification code, the notification, and/or the clarification for review. For example, the third module (112), upon receipt of the clarification from the third user device (122), may transmit the inputted information, the notification, and/or the clarification to the fourth user device (124) for review by the fourth user (e.g., an auditor).

receiving (514), from the fourth user device, a compliance review identifying an error associated with at least one of the classification code, the notification, and the clarification. For example, the fourth user, using the fourth user device (124), may review the inputted information and/or the generated notification to identify one or more errors associated with an inputted classification code, a narrative, the notification (e.g., comments associated with the inputted information and provided by the second user), and/or the clarification (e.g., comments associated with the notification and provided by the third user). The compliance review may be generated by the fourth user device (124) after review of the inputted information, the notification, and/or the clarification is complete. The compliance review may be transmitted from the fourth user device (124) to the load-balancing server (102) for processing by the first module (108), the second module (110), the third module (112), and/or the fourth module (114) (and/or any other system).

generating (516), based at least in part on the compliance review, a report. For example, the fourth module (114) may utilize information included in the compliance review (and/or any other information stored in the one or more memories (104), another database, and/or the like) to generate the report.

transmitting (518), to at least one of the first user device, the second user device, the third user device, and the fourth user device, the report. For example, upon generation, the report may be transmitted to the first user device (118), the second user device (120), the third user device (122), and/or the fourth user device (124) from the fourth module (114) for review by respective users. Additionally and/or alternatively, the report may be transmitted to another device external to the system (100). The report may also be stored in the one or more memories (104) and/or in another location.

In some embodiments, the report may include a variety of analytics, charts, or graphs, or summaries, and/or the like so that results of the compliance review may be clearly and/or accurately communicated to a diverse audience. Information included in the report may be sorted, modified, and/or otherwise manipulated by one or more users as described herein.

Figure 6:
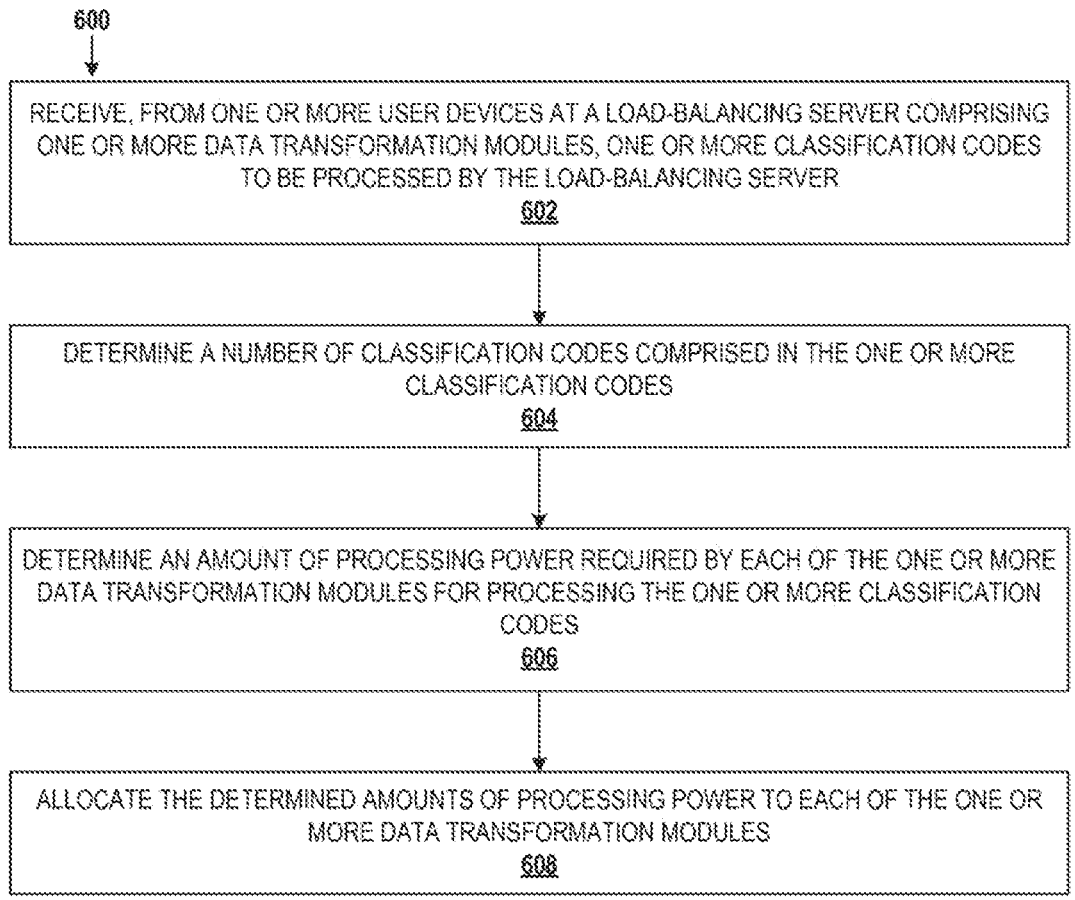
FIG. 6 represents the steps of the data processing executed by the fifth module, according to at least one embodiment.

FIG. 6 shows an exemplary of a method (600) for performing operations associated with the fifth module (116), by using the load-balancing server (102) (e.g., the first module (108), the second module (110), the third module (112), the fourth module (114), and/or the fifth module), the first user device (118), the second user device (120), the third user device (122), and/or the fourth user device (124). For example and without limitation, said method may include the steps of:

receiving (602), from one or more user devices at a load-balancing server comprising one or more data transformation modules, one or more classification codes to be processed by the load-balancing server. For example, multiple classification codes (and/or narratives and/or other information associated with provided medical services) may be received by one or more of the modules of the load-balancing system (102) from one or more user devices.

determining (604) a number of classification codes comprised in the one or more classification codes. For example, the fifth module (116) may count the number of incoming and/or inputted classification codes that are in the queue and ready to be processed.

determining (606) an amount of processing power required by each of the one or more data transformation modules for processing the one or more classification codes. For example, the fifth module (116) may determine minimum and/or maximum amounts of computing resources (e.g., processing power, memory, and/or the like) required, available, and/or currently utilized by each of the elements (e.g., the one or more memories (104), the one or more processors (106), the first module (108), the second module (110), the third module (112), the fourth module (114), and/or the fifth module (116)) of the load-balancing server (102).

allocating (608) the determined amounts of processing power to each of the one or more data transformation modules. For example, the fifth module (116) may allocate various computing resources to each of the one or more memories (104), the one or more processors (106), the first module (108), the second module (110), the third module (112), the fourth module (114), and/or the fifth module (116) so as to maximize efficiency and/or meet required needs of each element for processing of the incoming and/or inputted classification codes. In this manner, computing resources may be allocated based on volume, time of day, a predetermined duration of time, a period of time available for processing, a type of processing required, and/or any other factor. The fifth module (116) may also be configured to determine one or more factors associated with computing resources, such as an amount of processing and/or type of processing required by one or more of the first module (108), the second module (110), the third module (112), and/or the fourth module (114).

FIG. 7 shows an exemplary of a report (700) generated by the fourth module (114) based on any information associated with a provided medical service, as described herein.

In some embodiments, the report (700) generated by the fourth module (114) may include a name (702) associated with a provided medical service and/or a medical record such as a name of a first user (e.g., a medical provider), a second user (e.g., a coder), a third user (e.g., a supervisor), a fourth user (e.g., an auditor), and/or the like), and/or the like.

In some embodiments, the report (700) may include comprises a history (704) of all actions taken by any of the first user, the second user, the third user, and/or the fourth user during processing of the classification code. For example, the history (704) may include a timestamp associated with an input of a classification code and/or narrative, a timestamp associated with an input of a notification, a timestamp associated with an input of a clarification, a timestamp associated with a submission of a clarification code, a timestamp associated with a compliance review, and/or the like.

In some embodiments, the report (700) may include a listing of all inputted clarification codes (706), as well as a listing of all submitted clarification codes (708), a inputted narrative (710), an inputted notification (712), an inputted clarification (714), and/or the like. In some embodiments, the report (700) may further include an evaluation (716) of any user (e.g., the user whose name is listed in the name (702) column). (For example), the evaluation (716) may include an evaluation of a user's performance during processing of a classification code. The evaluation (716) may also include identification of one or more errors associated with processing of a classification code. For example, if a provided medical service was incorrectly coded, the fourth user may dente in the evaluation (716) column that the submitted classification code was incorrect, and may also provide a suggestion and/or a correct code for future and/or subsequent classification codes of similar provided medical services.

In some embodiments, the evaluation may also include information such as a score, a grade, comments, and/or notes associated with any aspect of the processing of a classification code. This information may be used by any of the users to improve processing of future and/or subsequent classification codes.

In some embodiments, the load-balancing server (102) is included in a system (100) comprising a plurality of user devices, each device of the plurality of user devices comprising at least an interactive HMI and/or an API and/or computer-executable instructions utilized by a user for performing particular operations, said plurality of user devices including at least a first user device (118) utilized by a medical service provider for inputting information associated with a provided medical service into the system, a second user device (120) utilized by a coder of medical services for reviewing said information associated with the provided medical service, a third user device (122) utilized by a supervisor for reviewing a notification, based on the review of information associated with the provided medical service, transmitted by the coder of medical services and eventually a fourth user device (124) utilized by an auditor for reviewing at least a clarification, transmitted by the supervisor from the review based on the notification emitted by the coder, and transmitting a compliance review to the load-balancing server (102) for processing.

While various implementations in accordance with the disclosed principles have been described above, it should be understood that they have been presented by way of example only, and are not limiting. Thus, the breadth and scope of the implementations should not be limited by any of the above-described exemplary implementations, but should be defined only in accordance with the claims and their equivalents issuing from this disclosure. Furthermore, the above advantages and features are provided in described implementations, but shall not limit the application of such issued claims to processes and structures accomplishing any or all of the above advantages.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

The present application describes various technical features and advantages with reference to the figures and/or various embodiments. Those skilled in the art will understand that the technical features of a given embodiment can in fact be combined with features of another embodiment unless explicitly stated otherwise, or unless the combination does not provide a solution to at least one of the technical problems mentioned in the present application. In addition, the technical features described in a given embodiment can be isolated from the other technical features of this embodiment unless explicitly stated otherwise.

Those skilled in the art will readily appreciate that the present invention encompasses embodiments in many specific forms without departing from the field of application of the claims. Consequently, the present embodiments must be considered as illustrations, but can be modified in the area defined by the scope of the appended claims, and the invention must not be limited to the details given above.

The invention claimed is:

1. A load-balancing server which intelligently allocates computing resources to a plurality of user devices across a computing network in response to an identified demand for the computing resources, the load-balancing server comprising:
   at least one memory storing instructions; and
   at least one processing device configured to execute the instructions, such that, when executed by the at least one processing device, the instructions cause the at least one processing device to perform operations comprising:
      establishing, using a communication unit, a digital communication connection over a computing network between the load-balancing server and the plurality of user devices;
      obtaining sensing information that correlates to an amount of computing resources available to a first user device of the plurality of user devices;
      receiving, via the computing network, a request for performing an operation, wherein said performing the operation requires utilization of the first user device;
      first determining, based on information comprised in the request, an amount of computing resources required by the first user device to perform the operation;
      second determining, based on the sensing information, the amount of computing resources available to the first user device; and
      allocating, based on the first determining and second determining steps, the amount of computing resources required by the first user device for performing the operation.

2. The load-balancing server according to claim 1, further comprising
   one or more modules operatively coupled to and/or utilizing one or more of the at least one memory and/or the at least one processing device of the load-balancing server for performing particular operations associated with real-time inputting and reviewing, as well as auditing and/or reporting, of information.

3. The load-balancing server according to claim 1, further comprising
   one or more of a first module, a second module, a third module, a fourth module, a fifth module,
   wherein each of said one or more of said first module, said second module, said third module, said fourth module, said fifth module comprising specially-purposed hardware and computer-executable instructions for performing particular operations associated with real-time inputting and reviewing, as well as auditing and/or reporting of information.

4. The load-balancing server according to claim 3, further comprising
   a queue memory for storing classification codes, transmitted at least by the first module, placed in queue and waiting to be processed.

5. The load-balancing server according to claim 4, wherein the fifth module of the load-balancing server is connected to the queue memory and comprises a module for counting a number of classification codes in queue and for transmitting said number to an alert module of said fifth module configured to, using at least a predetermined threshold value, determine if the number of classification codes that have been placed in the queue meets or exceeds said predetermined threshold value in order to trigger the allocating the amount of computing resources.

6. The load-balancing server according to claim 5, wherein the fifth module evaluates an amount, based on said predetermined threshold value, of additional processing power required by the first module or the second module or the third module and/or the fourth module for processing inputted classification codes in queue, the amount of additional processing power being respectfully allocated, using hardware and software-based communication devices of the load-balancing server, to one or more of the first module, the second module, the third module and the fourth module.

7. The load-balancing server according to claim 1, wherein said allocating the amount of computing resources comprises flipping a switch, adjusting processing power, adjusting memory size, partitioning a memory element, or controlling one or more input and/or output devices.

8. The load-balancing server according to claim 3, wherein the fifth module comprises specially-purposed hardware for monitoring performance of each element of the load-balancing server and for responding to computing resource needs of each element.

9. The load-balancing server according to claim 3, wherein the fifth module comprises one or more hardware and software-based communication devices configured to enable communication between said fifth module and at least one of the first module, the second module, the third module, and the fourth module.

10. The load-balancing server according to claim 1, wherein the load-balancing server comprises a set of modules for transforming data from one form to another form, and for enabling said load-balancing server to communicate with the plurality of user devices, the at least one memory, or other devices or systems.

11. The load-balancing server according to claim 1, wherein each device of the plurality of user devices comprising at least an interactive HMI or an API or computer-executable instructions utilized by a user for performing particular operations, said plurality of user devices including at least a first user device configured to be utilized by a medical service provider for inputting information associated with a provided medical service into a system, a second user device configured to be utilized by a coder of medical services to review said information associated with the provided medical service, a third user device configured to be utilized by a supervisor to review a notification, based on the review of information associated with the provided medical service, transmitted by the coder of medical services, and a fourth user device configured to be utilized by an auditor to review at least a clarification, transmitted by the supervisor from the review based on the notification emitted by the coder, and which transmits a compliance review to the load-balancing server.

12. A system, comprising:
a load-balancing server configured to intelligently allocate computing resources to a plurality of user devices across a computing network in response to an identified demand for the computing resources,
the load-balancing server including;
at least one memory storing instructions; and
at least one processing device configured to execute the instructions, such that, when executed by the at least one processing device, the instructions cause the at least one processing device to perform operations comprising:
establishing, using a communication unit, a digital communication connection over a computing network between the load-balancing server and the plurality of user devices in the computing network;
obtaining sensing information that correlates to an amount of computing resources available to a first user device of the plurality of user devices;
receiving, via the computing network, a request for performing an operation, wherein said performing the operation requires utilization of the first user device;
first determining, based on information comprised in the request, an amount of computing resources required by the first user device to perform the operation;
second determining, based on the sensing information, an amount of computing resources available to the first user device; and
allocating, based on the first determining and second determining steps, the amount of computing resources required by the first user device for performing the operation,
wherein said load-balancing server comprises devices configured for real-time inputting and reviewing, auditing and/or reporting, of classification codes associated with provided medical services.

13. The system according to claim 12, further comprising:
an I/O (input/output) module;
at least one memory for storing data;
at least database API; and
at least a data treatment processor.

14. The system according to claim 12,
wherein the plurality of user devices further include a second user device; a third user device; and a fourth user device, each of said plurality of user devices comprising at least one memory for storing data, at least one processor for executing computer-executable instructions related to medical services, input and/or output devices for enabling one or more users to interact with each user device, and one or more memories.

15. The system according to claim 12, wherein each of the plurality of user devices further comprises:
at least one of a keyboard, mouse, a touchpad, touch screen, camera, or a microphone;
a radio frequency identification (RFID) scanner;
a display or monitor; and
a speaker,
wherein each of the plurality of user devices is configured to receive input from and/or display output to one or more users and hardware for communicating between other user devices and/or with the load-balancing server.

16. The system according to claim 12, wherein the load-balancing server and/or any of the plurality of user devices include one or more radio transceivers or chips or analog front end (AFE) units or antennas or processing units or memory or other logic, and/or other components to implement communication (wired or wireless) protocols and related functionality for facilitating communication between the load-balancing server and/or any of the plurality of user devices.

17. The system according to claim 14, wherein each of the plurality of user devices communicates with the load-balancing server via one or more networks.

18. The system according to claim 17, wherein said one or more networks include any wireless or wired communications network that facilitates communication between the load-balancing server, the first user device, the second user device, the third user device, or the fourth user device.

19. The system according to claim 17, further comprising
an interactive interface of the first user device adapted to input a classification code associated with a provided medical service and then to transmit said classification code from the first user device to a first module of the load-balancing server via the one or more networks for storing in queue.

20. The system according to claim 19, wherein the first module transmits the classification code to the second user device via the one or more networks for review by a second user on the second user device to review the classification code for completeness or accuracy.

21. The system according to claim 19, wherein one or more of the first module of the load-balancing server, the second user device, a second module of the load-balancing server, and the third user device, a third module of the load-balancing server, or the fourth user device each comprise a set of tools capable of being configured by computer-executable instructions for automatically performing analyses on notifications or classification codes.

22. The system according to claim 21, wherein said set of tools comprises at least a text or code analysis module, a recommendation module, and a correction module, said text or code analysis module configured to identify errors in a given notification or classification code and to produce an error report containing said errors, said recommendation module for analyzing the error report and producing a recommendation file containing a set of instructions to be executed for correcting the errors identified in the error report, said correction module being configured to read the recommendation file and to modify said notification and/or classification code.

23. The system according to claim 22, wherein the first module of the load-balancing server and the second user device, are each configured to review the classification code that has been modified prior to submission.

24. The system according to claim 21, wherein the second user device further comprises a set of tools for enabling a second user to input a notification associated with an inputted classification code, said notification including information associated with a review of the inputted classification code.

25. The system according to claim 22, wherein the second user device transmits said notification to the second module of the load-balancing server, and said second module transmits said notification to the third user device for review by a third user.

26. The system according to claim 25, wherein the third user utilizes one or more output devices of the third user device to review the notification, said one or more output devices generating a report on the review of said notification.

27. The system according to claim 22, wherein the second module and the third user device are each configured to review the notification code that has been modified prior to transmission to the first user device.

28. The system according to claim 22, wherein the load-balancing server is further configured to avoid transmission of the notification to the first user device until said notification has been indicated as approved by a third user.

29. The system according to claim 22, wherein one or more of the second module of the load-balancing server and the third user device, the third module of the load-balancing server, and the fourth user device also includes a data module comprising computer-executable instructions for retrieving, receiving and/or otherwise assessing information stored in one or more databases operatively coupled to the system, during an analysis of the classification code.

30. The system according to claim 29, wherein the third user device further comprises an interactive interface for allowing the third user to input a clarification including information associated with the notification, during or after review of the notification.

31. The system according to claim 30, wherein said clarification is transmitted from the third user device to the second module or another module of the load-balancing server for distribution to one or more user devices, or is transmitted directly to the second user device for review by the second user prior to transmission of the notification to the first user device.

32. The system according to claim 30, wherein after a submission of the classification code to billing and/or insurance processing, the first module, second module, any of the first user device, the second user device, or the third user device transmits the classification code that has been inputted, the classification code that has been submitted, any information and/or narratives associated with the classification code and/or the provided medical service, the notification, the clarification to the third module or a fourth module.

33. The system according to claim 29, wherein the classification code is randomly selected from an amassed listing or database of submitted classification codes by the fourth user, using the fourth user device.

34. The system according to claim 29, wherein after auditing information associated with the classification code, one or more output devices of the fourth user device generates a user-initiated compliance review report that includes information associated with completeness, accuracy, and/or compliance of the classification code that has been submitted, and an evaluation of a performance of users involved in the coding processes.

35. The system according claim 34, wherein the user-initiated compliance review is transmitted by the fourth user device or the third module for distribution to any of the first user device, the second user device, or the third user device, for respective user review.

36. The system according to claim 19,
wherein a fourth module of the load-balancing server is configured to generate a report that includes a number of inputted classification codes, a number of submitted classification codes, a number of notifications, a number of clarifications,
wherein the information included in said report is sorted based on a medical provider type, a classification code, a disease diagnosis, a treatment type, a hospital, a notification type, a clarification type, or a search history.

37. The system according to claim 36, wherein the report generated by the fourth module, is transmitted to any one or more of the plurality of user devices and/or to another system external to the system for further processing.

38. The system according to claim 37, wherein the report generated by the fourth module includes a history comprising at least a timestamp associated with an input of a classification code and/or narrative, a timestamp associated with an input of a notification, a timestamp associated with an input of a clarification, a timestamp associated with a submission of a clarification code, and a timestamp associated with a compliance review.

39. The system according to claim 12, wherein the load-balancing server is configured, to use a control API (Application Programming Interface) for processing a high volume of classification codes inputted by a large number of users.

40. The system according to claim 39, wherein a fifth module of the load-balancing server is configured, by said control API, to manage the allocation of computing resources as needed by particular elements of the load-balancing server.

* * * * *